US005231103A

United States Patent [19]
Matzke et al.

[11] Patent Number: 5,231,103
[45] Date of Patent: Jul. 27, 1993

[54] QUINOLIN-2-YL-METHOXYBENZYLHY-DROXYUREAS

[75] Inventors: Michael Matzke; Klaus-Helmut Mohrs, both of Wuppertal; Siegfried Raddatz; Romanis Fruchtmann, both of Cologne; Armin Hatzelmann, Burscheid; Christian Kohlsdorfer, Erftstadt; Reiner Müller-Peddinghaus, Bergisch Gladbach; Pia Theisen-Popp, Aachen, all of Fed. Rep. of Germany

[73] Assignee: Bayer Aktiengesellschaft, Leverkusen, Fed. Rep. of Germany

[21] Appl. No.: 917,641

[22] Filed: Jul. 21, 1992

[30] Foreign Application Priority Data

Jul. 31, 1991 [DE] Fed. Rep. of Germany ....... 4125270

[51] Int. Cl.$^5$ ..................... A61K 31/47; C07D 215/14
[52] U.S. Cl. .................................... 514/312; 514/311; 546/153; 546/155; 546/175; 546/176
[58] Field of Search ............... 514/311, 312; 546/175, 546/153, 155, 176

[56] References Cited

U.S. PATENT DOCUMENTS 5,091,392  2/1992  Raddatz et al. ..................... 546/175

FOREIGN PATENT DOCUMENTS 0414019  8/1990  European Pat. Off. .
0416609  9/1990  European Pat. Off. .
8904299  5/1989  World Int. Prop. O. .

OTHER PUBLICATIONS

Beilstein 4(3), p. 1861 (1949).
Beilstein 12, pp. 437–446.
C. King, J. Org. Chem., 1960, pp. 352–356.
Franz Effenberger, *Chem. Ber.*, 1964, pp. 1576–1583.
Dr. H. Ulrich, *Angewandte Chemie*, Aug. 21, 1966, pp. 761–788.
CAS 38 459-58-4.
Gunther E. Jeromin, Chem. Ber., 1987, pp. 649–651.
Pierre Borgeat, *Proc. Nat. Acad. Sci USA*, May 1979, pp. 2148–2152.
Houben-Weyl VIII, 1952, p. 128.

*Primary Examiner*—C. Warren Ivy
*Assistant Examiner*—James H. Turnipseed
*Attorney, Agent, or Firm*—Sprung Horn Kramer & Woods

[57] ABSTRACT

The novel quinolin-2-yl-methoxybenzylhydroxyureas can be prepared by reaction of appropriate ketones with hydroxylamine and reduction of the ketoximes and subsequent reaction with isocyanates. The new substances can be employed as active substances in medicaments.

9 Claims, No Drawings

QUINOLIN-2-YL-METHOXYBENZYLHYDROX- YUREAS

The invention relates to quinolin-2-yl-methoxybenzylhydroxyureas, their derivatives, a process for their preparation and their use in medicaments.

It is already known that indole-, benzofuran- and benzothiophenehydroxyureas and their derivatives have a lipoxygenase-inhibiting action [cf. EP 416,609 A2]. In addition, furan- and pyrroloxime-hydroxyureas are described in the publication EP 388,429 (PCT WO89/04299).

The present invention relates to quinolin-2-yl-methoxybenzylhydroxyureas of the general formula (I)

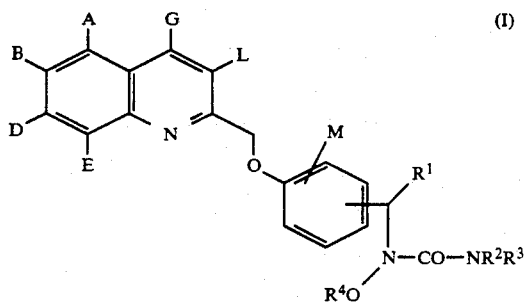

(I)

in which

A, B, D, E, G, L and M are identical or different and represent hydrogen, hydroxyl, halogen, cyano, carboxyl, nitro, trifluoromethyl, trifluoromethoxy or represent straight-chain or branched alkyl or alkoxy each having up to 8 carbon atoms, or represent aryl having 6 to 10 carbon atoms, which is optionally substituted by halogen, hydroxyl, nitro or cyano, $R^1$ represents cycloalkyl or -alkenyl having 3 to 12 carbon atoms, represents straight-chain or branched alkyl having up to 8 carbon atoms, $R^2$ and $R^3$ are identical or different and represent hydrogen, straight-chain or branched alkyl having up to 8 carbon atoms or represent phenyl or benzyl, or $R^2$ represents hydrogen and $R^3$ represents a group of the formula $-SO_2R^5$, in which $R^5$ denotes straight-chain or branched alkyl having up to 8 carbon atoms, which is optionally substituted by halogen, nitro, cyano, hydroxyl, trifluoromethyl or by aryl having 6 to 10 carbon atoms, or denotes aryl having 6 to 10 carbon atoms, which is monosubstituted to trisubstituted by identical or different substituents from the series comprising halogen, nitro, cyano, hydroxyl, straight-chain or branched alkyl, alkylthio or alkoxy having up to 8 carbon atoms, trifluoromethyl and trifluoromethoxy, $R^4$ represents hydrogen or straight-chain or branched acyl having up to 8 carbon atoms or benzoyl, and their salts.

In the context of the present invention, physiologically acceptable salts are preferred. Physiologically acceptable salts of the quinolin-2-yl-methoxybenzylhydroxyureas and their derivatives can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Salts in the context of the present invention can additionally be salts of metals, preferably of univalent metals, such as alkali metals, and ammonium salts. Sodium, potassium and ammonium salts are preferred.

The compounds according to the invention exist in stereoisomeric forms which behave either as image and mirror image (enantiomers) or which do not behave as image and mirror image (diastereomers). The invention relates both to the antipodes and to the racemic modifications as well as the diastereomer mixtures. Like the diastereomers, the racemic modifications can also be separated into the stereoisomerically uniform constituents in a known manner [cf. E. L. Eliel, Stereochemistry of Carbon Compounds, McGraw Hill, 1962].

Preferred compounds of the general formula (I) are those in which

A, B, D, E, G, L and M are identical or different and represent hydrogen, hydroxyl, fluorine, chlorine, bromine, carboxyl, nitro, trifluoromethyl, trifluoromethoxy or represent straight-chain or branched alkyl or alkoxy each having up to 6 carbon atoms, or represent phenyl which is optionally substituted by fluorine, chlorine, bromine, hydroxyl, nitro or cyano, $R^1$ represents cyclobutyl, cyclopentyl, cyclohexyl, cycloheptyl or cyclooctyl, represents straight-chain or branched alkyl having up to 6 carbon atoms, $R^2$ and $R^3$ are identical or different and represent hydrogen or straight-chain or branched alkyl having up to 6 carbon atoms, or $R^2$ represents hydrogen and $R^3$ represents a group of the formula $-SO_2R^5$, in which $R^5$ denotes straight-chain or branched alkyl having up to 6 carbon atoms, which is optionally substituted by fluorine, chlorine, nitro, cyano, hydroxyl or by phenyl, or denotes phenyl which is optionally monosubstituted or disubstituted by identical or different substituents from the series comprising fluorine, chlorine, bromine, nitro, cyano, hydroxyl, straight-chain or branched alkyl, alkylthio or alkoxy having up to 6 carbon atoms, trifluoromethyl and trifluoromethoxy, $R^4$ represents hydrogen or straight-chain or branched acyl having up to 6 carbon atoms or benzoyl and their salts.

Particularly preferred compounds of the general formula (I) are those in which

A, B, D, E, G, L and M are identical or different and represent hydrogen, hydroxyl, fluorine, chlorine, bromine or straight-chain or branched alkyl having up to 4 carbon atoms, $R^1$ represents cyclopentyl, cyclohexyl or cycloheptyl, represents straight-chain or branched alkyl having up to 4 carbon atoms, $R^2$ and $R^3$ are identical or different and represent hydrogen or straight-chain or branched alkyl having up to 4 carbon atoms, or $R^2$ represents hydrogen, and $R^3$ represents a group of the formula $-SO_2R^5$, in which $R^5$ denotes straight-chain or branched alkyl having up to 4 carbon atoms, which is optionally substituted by fluorine, chlorine or phenyl, or denotes phenyl which is optionally substituted by fluorine, chlorine, bromine or by straight-chain or branched alkyl having up to 4 carbon atoms, $R^4$ represents hydrogen or straight-chain or branched acyl having up to 4 carbon atoms or benzoyl and their salts.

Very particularly preferred compounds of the general formula (I) are those in which A, B, D, E, G, L and M represent hydrogen. Compounds are also very particularly preferred in which the radical —HC($R^1$)-N(O$R^4$)(CO—N$R^2R^3$) is in the 4-position relative to the quinolylmethoxy radical.

In addition, a process for the preparation of the compounds of the general formula (I) according to the invention has been found, which is characterised in that compounds of the general formula (II)

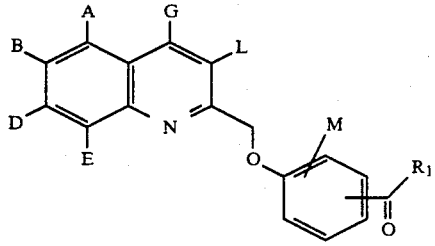
(II)

in which A, B, D, E, G, L, M and $R^1$ have the abovementioned meaning, are first reacted in inert solvents, if appropriate in the presence of a base, with hydroxylamine hydrochloride to give the ketoximes of the general formula (III)

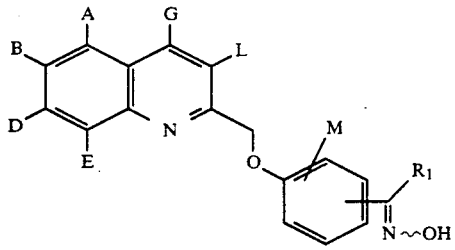
(III)

in which A, B, D, E, G, L, M and $R^1$ have the abovementioned meaning, then these are converted in inert solvents, if appropriate in the presence of acids, using reducing agents to the hydroxylamines of the general formula (IV)

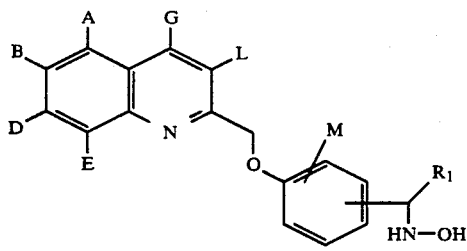
(IV)

in which A, B, D, E, G, L, M and $R^1$ have the abovementioned meaning, and in a last step, in the case in which $R^2$ and $R^3$=H, these are reacted with ($C_1$-$C_6$)-trialkylsilyl isocyanates, preferably with trimethylsilyl isocyanate, and, in the case in which $R^2$=H and $R^3\neq$H, with isocyanates of the general formula (V)

$$T-N=C=O \qquad (V)$$

in which T represents ($C_1$-$C_8$)-alkyl, phenyl or the radical —$SO_2R^5$, in which, $R^5$ has the abovementioned meaning, or hydroxylamines of the general formula (IV) are first converted with gaseous HCl and then with phosgene to the compounds of the general formula (VI)

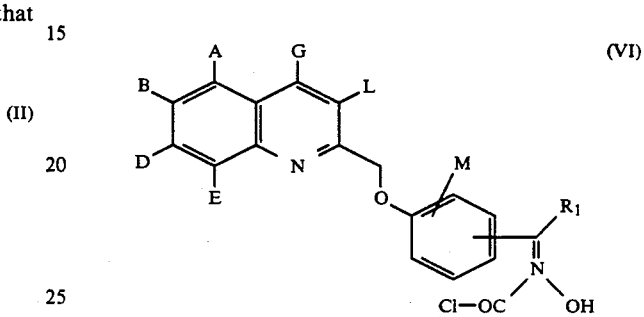
(VI)

in which A, B, D, E, G, L, M and $R^1$ have the abovementioned meaning, in inert solvents and these are subsequently reacted, if appropriate in inert solvents, with amines of the general formula (VII)

$$HNR^2R^3 \qquad (VII)$$

in which $R^2$ and $R^3$ are identical or different and have the abovementioned meaning, and, in the case in which $R^4\neq$H, compounds of the general formula (Ia)

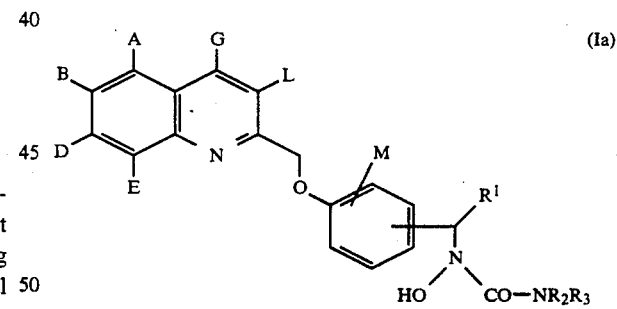
(Ia)

which A, B, D, E, G, L, M, $R^1$, $R^2$ and $R^3$ have the abovementioned meaning, are acylated using customary acylating agents, preferably using acid halides of the general formula (VIII)

$$R^{4'}-CO-X \qquad (VIII)$$

in which $R^{4'}$ has the abovementioned meaning of $R^4$, but does not represent hydrogen and X represents a leaving group customary in acylating agents, preferably chlorine, in inert solvents, if appropriate in the presence of a base.

The process according to the invention can be illustrated by way of example by the following equation:

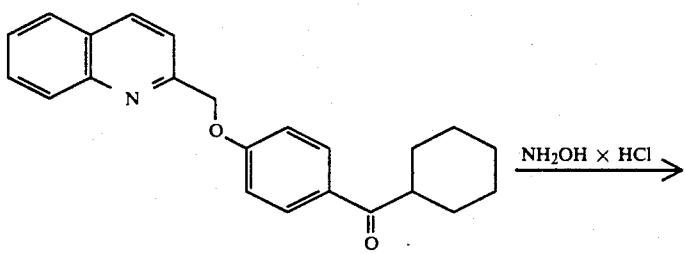

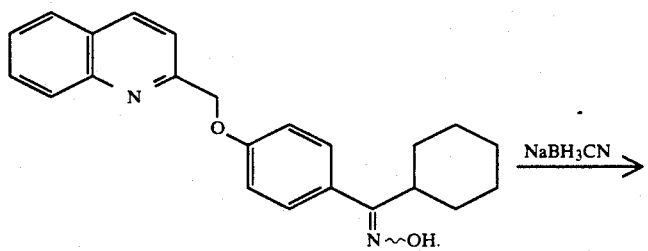

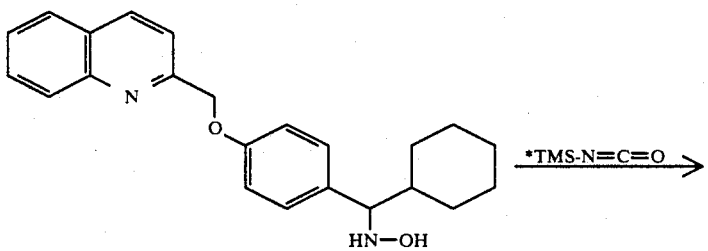

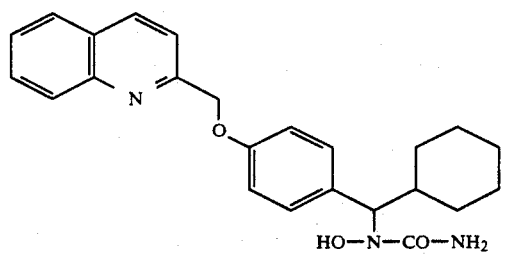

*TMS = Trimethylsilyl

Suitable solvents for the reaction with hydroxylamine hydrochloride are the customary organic solvents which do not change under the reaction conditions. These preferably include alcohols such as methanol, ethanol, propanol or isopropanol or hydrocarbons such as benzene, toluene, xylene, hexane, cyclohexane or mineral oil fractions, or acetonitrile, dimethyl sulphoxide or dimethylformamide. Methanol and ethanol are preferred.

Suitable bases are organic amines (trialkyl($C_1$–$C_6$)amines) such as, for example, triethylamine or heterocycles such as pyridine, methylpiperidine, piperidine or morpholine. Pyridine is preferred.

The base is employed in an amount of from 1 mol to 20 mol, preferably from 5 mol to 10 mol, relative to 1 mol of the compound of the general formula (II).

The reaction is carried out in a temperature range from 0° C. to +80° C., preferably at room temperature.

Suitable reducing agents for the reduction of the oximes of the general formula (III) are in general hydrides, such as complex borohydrides and borohydride amine complexes or aluminum hydrides. Those preferably employed here are sodium borohydride, sodium cyanoborohydride or borane pyridine complex. Sodium cyanoborohydride is particularly preferred.

Suitable solvents in this case are all inert organic solvents which do not change under the reaction conditions. These preferably include alcohols such as methanol, ethanol, propanol or isopropanol, or ethers such as diethyl ether, dioxane, tetrahydrofuran, glycol dimethyl ether or diethylene glycol dimethyl ether or amides such as hexamethylphosphoric triamide or dimethylformamide, or acetic acid. It is also possible to use mixtures of the solvents mentioned. Methanol is preferred.

The reduction with sodium cyanoborohydride is in general carried out in the presence of protonic acids. These preferably include inorganic acids such as, for example, hydrochloric acid or sulphuric acid, or organic carboxylic acids having 1 to 6 C atoms, optionally substituted by fluorine, chlorine and/or bromine, such as, for example, acetic acid, trifluoroacetic acid, trichloroacetic acid or propionic acid, or sulphonic acids having $C_1$–$C_4$-alkyl radicals or having aryl radicals, such as, for example, methanesulphonic acid, ethanesulphonic acid, benzenesulphonic acid or toluenesulphonic acid.

Acids employed for all other process steps are in general also mineral acids. Those preferably employed here are hydrochloric acid, hydrobromic acid, sulphuric acid, phosphoric acid or else mixtures of the acids mentioned. Hydrochloric acid is always preferred.

Depending on the particular reactants, the acids are added in the amount required to establish a pH of 3.

The reduction is in general carried out in a temperature range from 0° C. to +60° C., preferably at room temperature.

The reaction is in general carried out at normal pressure. However, it is also possible to carry out the process at reduced pressure or elevated pressure (for example in a range from 0.5 to 5 bar).

The reaction of the compounds of the general formula (IV) with the isocyanates is carried out in customary organic solvents which do not change under the reaction conditions. These preferably include ethers such as diethyl ethers, dioxane, tetrahydrofuran, glycol dimethyl ether, or hydrocarbons such as benzene, toluene, xylene, hexane, cyclohexane or mineral oil fractions, or halogenohydrocarbons such as dichloromethane, trichloromethane, tetrachloromethane, dichloroethylene, trichloroethylene or chlorobenzene, or ethyl acetate, triethylamine, pyridine, dimethyl sulphoxide, dimethylformamide, hexamethylphosphoric triamide, acetonitrile, acetone or nitromethane. It is also possible to use mixtures of the solvents mentioned. Dioxane and methylene chloride are preferred.

The reactions in general proceed in a temperature range from 0° C. to +150° C., preferably from +20° C. to +120° C.

Suitable solvents for the reaction with the isocyanates are the abovementioned ethers, hydrocarbons or halogenohydrocarbons or their mixtures, preferably ethers such as, for example, diethyl ether or tetrahydrofuran, or halogenohydrocarbons such as, for example, methylene chlorine or chloroform. Methylene chloride is particularly preferred.

The reaction with sulphonyl isocyanates is in general carried out in a temperature range from −78° C. to +120° C., preferably from −50° C. to +100° C.

The reaction with the isocyanate is in general carried out at normal pressure. However, it is also possible to work at elevated pressure or at reduced pressure (for example in a range from 0.5 to 5 bar).

In general, 1 to 3 mol, preferably 1 to 2 mol, particularly preferably 1 mol, of isocyanate is employed, relative to 1 mol of the compound of the general formula (IV).

The alkyl, phenyl and silyl isocyanates of the general formula (V) are known or can be prepared by a customary method [cf. for example Beilstein 4 (3), 1861; Beilstein 12, 437].

The sulphonyl isocyanates (VI) are known from the literature [cf. C. King, J. Org. Chem. 25, 352 (1960); F. Effenberger, R. Gleiter, Chem. Ber. 97, 1576 (1964); H. Ulrich, A. A. R. Sayigh, Angew. Chem. 78, 761 (1966); Houben-Weyl VIII, 128].

The reaction of the compounds of the general formula (VI) with ammonia ($R^2/R^3=H$), ammonium chloride or the amines of the general formula (VII) is carried out either in one of the abovementioned solvents or using the respective amine component as a solvent, preferably using the respective amine in excess, in a temperature range from −10° C. to +50° C. and at normal pressure.

The compounds of the general formula (VI) are new and can be prepared by the abovementioned process.

The amines of the general formula (VII) are known [cf. Houben-Weyl's "Methoden der organischen Chemie" (Methods of Organic Chemistry), Vol. XI/1 and XI/2].

Leaving group in the acylating agents of the general formula (VIII) in general means radicals such as, for example, chlorine, bromine, thiazolyl, methanesulphonyloxy or aryloxy. Chlorine is preferred. The acylating agents are known from the literature.

The acylation in general proceeds in a temperature range from 0° C. to +120° C., preferably at +30° C. to +90° C., in one of the abovementioned solvents, preferably in pyridine and at normal pressure.

Suitable bases for the acylation are inorganic or organic bases. These preferably include alkali metal hydroxides such as, for example, sodium hydroxide or potassium hydroxide, alkaline earth metal hydroxides such as, for example, barium hydroxide, alkali metal carbonates such as sodium carbonate or potassium carbonate, alkaline earth metal carbonates such as calcium carbonate, or organic amines (trialkyl($C_1$-$C_6$)amines) such as triethylamine, or heterocycles such as pyridine, methylpiperidine, piperidine or morpholine. Triethylamine is preferred.

The compounds of the general formula (Ia) are likewise new and can be prepared by the abovementioned process.

Some of the compounds of the general formula (II) are known or, in the case in which $R^1$ represents cycloalkyl, are new and can be prepared, for example, by etherifying compounds of the general formula (IX)

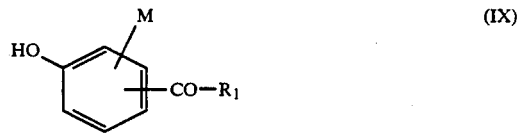

(IX)

in which M and $R^1$ have the abovementioned meaning, in inert solvents, if appropriate in the presence of a base, with compounds of the general formula (X)

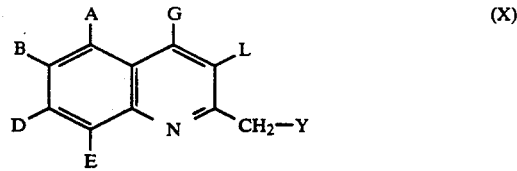

(X)

in which A, B, D, E, G and L have the abovementioned meaning and Y represents halogen, preferably chlorine or bromine.

The etherification can be carried out in inert organic solvents, if appropriate in the presence of a base. Solvents for the etherification can be inert organic solvents which do not change under the reaction conditions. These preferably include ethers such as, for example, dioxane, tetrahydrofuran or diethyl ether, halogenohydrocarbons such as dichloromethane, trichloromethane, tetrachloromethane, 1,2-dichloroethane or trichloroethylene, hydrocarbons such as benzene, xylene, toluene, hexane, cyclohexane or mineral oil fractions, nitromethane, dimethylformamide, acetonitrile, acetone or hexamethylphosphoric triamide. It is also possible to employ mixtures of the solvents.

Bases which can be employed for the etherification are inorganic or organic bases. These preferably include alkali metal hydroxides such as, for example, sodium hydroxide or potassium hydroxide, alkaline earth metal hydroxides such as, for example, barium hydroxide, alkali metal carbonates such as sodium carbonate or potassium carbonate, alkaline earth metal carbonates such as calcium carbonate, or organic amines (trialkyl($C_1$-$C_6$)amines) such as triethylamine, or heterocycles such as pyridine, methylpiperidine, piperidine or morpholine.

It is also possible to employ as bases alkali metals such as sodium and its hydrides, such as sodium hydride.

The etherification is in general carried out in a temperature range from 0° C. to +150° C., preferably from +10° C. to +100° C.

The etherification is in general carried out at normal pressure. However, it is also possible to carry out the process at reduced pressure or elevated pressure (for example in a range from 0.5 to 5 bar).

In general, 0.5 to 5, preferably 1 to 2, mol of halide are employed, relative to 1 mol of the compound of the general formula (IX). The base is in general employed in an amount of from 0.5 to 5 mol, preferably from 1 to 3 mol, relative to the halide (X).

The compounds of the general formulae (IX) and (X) are known per se or can be prepared by a customary method [cf. CAS 38 459-58-4 and Chem. Ber. 120, 649 (1987)].

The compounds of the general formulae (III) and (IV) are largely new (in particular if $R^1$ represents cycloalkyl) and can be prepared by the abovementioned process.

The quinolin-2-yl-methoxybenzylhydroxyureas according to the invention and their derivatives can be employed as active substances in medicaments. The substances can act as inhibitors of enzymatic reactions in the context of arachidonic acid metabolism, in particular of lipoxygenase.

They are thus preferred for the treatment and prevention of diseases of the airways such as allergies/asthma, bronchitis, emphysema, shock lung, pulmonary hypertension, inflammations/rheumatism and oedemas, thromboses and thromboembolisms, ischaemias (peripheral, cardiac and cerebral circulatory disorders), cardiac and cerebral infarcts, angina pectoris, arteriosclerosis, in tissue transplants, dermatoses such as psoriasis, inflammatory dermatoses and for cytoprotection in the gastrointestinal tract.

The quinolin-2-yl-methoxybenzylhydroxyureas according to the invention and their derivatives can be used both in human medicine and also in veterinary medicine.

The pharmacological actions of the substances according to the invention are determined by the following method:

As a measure of lipoxygenase inhibition, the release of leukotriene $B_4$ ($LTB_4$) in polymorphonuclear human leucocytes (PMN) after addition of substances and Ca ionophore was determined by means of reverse phase HPLC according to Borgeat, P. et al., Proc. Nat. Acad. Sci., 76, 2148-2152 (1979).

In Table 1, the values for some compounds according to the invention obtained by this test are shown by way of example:

TABLE 1

| Example No. | 5-LO $IC_{50}$ ($\mu$mol/l) |
|---|---|
| 1 | 0.25 |
| 2 | 1.2 |

The present invention also includes pharmaceutical preparations which, in addition to inert, non-toxic, pharmaceutically suitable auxiliaries and excipients, contain one or more compounds of the general formula (I), or which consist of one or more active substances of the formula (I), and processes for the production of these preparations.

The active substances of the formula (I) should be present in these preparations in a concentration from 0.1 to 99.5% by weight, preferably from 0.5 to 95% by weight of the total mixture.

In addition to the active substances of the formula (I), the pharmaceutical preparations can also contain other pharmaceutical active substances.

The abovementioned pharmaceutical preparations can be prepared in a customary manner by known methods, for example using the auxiliary or excipient or auxiliaries or excipients.

In general, it has proven advantageous to administer the active substance or substances of the formula (I) in total amounts of about 0.01 to about 100 mg/kg, preferably in total amounts of about 1 mg/kg to 50 mg/kg of body weight every 24 hours, if appropriate in the form of several individual doses, to achieve the desired result.

However, it may also be advantageous to depart from the amounts mentioned, in particular depending on the type and the body weight of the subject to be treated, on individual behaviour towards the medicament, the nature and severity of the disease, the manner of preparation and administration, and the time or interval at which administration takes place.

Starting compounds

EXAMPLE I

4-Methoxyphenyl cyclohexyl ketone

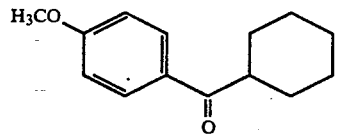

42.6 g (0.291 mol) of cyclohexanecarbonyl chloride and then 30 g (0.277 mol) of anisole are added dropwise at room temperature to a suspension of 44.4 g (0.33 mol) of aluminium chloride in 120 ml of dichloroethane. The reaction mixture is stirred for 1 h and allowed to stand overnight. For working up, the mixture is poured into ice-water and the aqueous phase is extracted with dichloromethane. The organic phase is washed with 1N NaOH and water, dried over sodium sulphate and concentrated in vacuo.

Yield: 58.6 g (97% of theory)

M.p.: 59°-62° C.

EXAMPLE II

4-Hydroxyphenyl cyclohexyl ketone

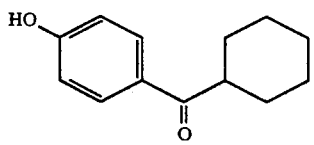

A solution of 11 g (50.4 mmol) of 4-methoxyphenyl cyclohexyl ketone in 730 ml of dichloromethane p.a. is treated at −70° C. under argon with 101 ml of a 1M solution of boron tribromide (101 mmol) in dichloromethane and then left at room temperature for 18 h. It is concentrated in vacuo, the residue is taken up with 500 ml of ethanol and 80 ml of water and the mixture is heated under reflux for 3 h. After concentration in vacuo, the residue is taken up in dichloromethane, and the organic phase is washed with water, dried over sodium sulphate and concentrated to dryness in vacuo. The crude product is chromatographed on silica gel using dichloromethane/methanol (20:1).

Yield: 7.9 g (76.7% of theory)
M.p.: 81°–84° C.

EXAMPLE III 4-(Quinolin-2-yl-methoxy)phenyl cyclohexyl ketone

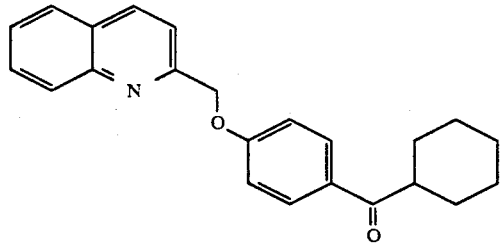

7.85 g (38.4 mmol) of 4-hydroxyphenyl cyclohexyl ketone are heated under reflux for 2 h after addition of 12 g (86.8 mmol) of potassium carbonate and 200 ml of dimethylformamide. 8.54 g (39.9 mmol) of 2-chloromethylquinoline hydrochloride are then added at room temperature. The reaction mixture is stirred at 100° C. for 7 h and subsequently concentrated in vacuo. The residue is taken up in dichloromethane, and the organic phase is washed with water, dried over sodium sulphate and concentrated in vacuo. A column chromatographic purification on silica gel using dichloromethane/methanol (50:1) follows.

Yield: 12.3 g (92.7% of theory)
M.p.: 103°–104° C.

EXAMPLE IV 4-(Quinolin-2-yl-methoxy)phenyl cyclohexyl ketoxime

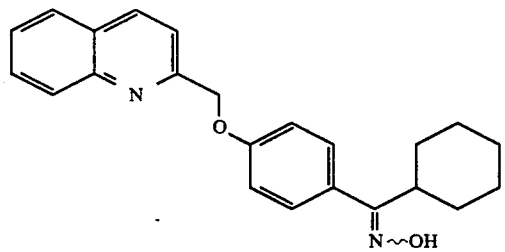

A solution of 15.9 g (46 mmol) of 4-(quinolin-2-yl-methoxy)phenyl cyclohexyl ketone in 100 ml of ethanol and 33 ml of pyridine is stirred at room temperature for 18 h after addition of 4.77 g (68.6 mmol) of hydroxylamine hydrochloride. For working up, the mixture is concentrated in vacuo and the residue is taken up in dichloromethane. The organic phase is washed with water, dried over sodium sulphate and concentrated to dryness in vacuo.

Yield: 11.4 g (68.8% of theory) of colourless crystals
M.p.: 167°–171° C.

EXAMPLE V

N-[4-(Quinolin-2-yl-methoxy)phenyl-cyclohexyl]methylhydroxylamine

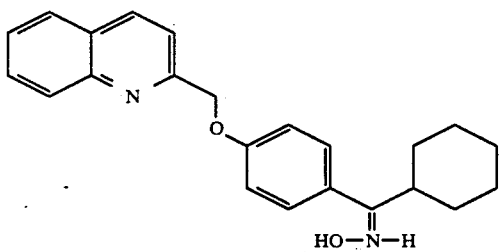

A mixture of 7 g (19.4 mmol) of 4-(quinolin-2-yl-methoxy)phenyl cyclohexyl ketoxime and 860 mg (13.7 mmol) of sodium cyanoborohydride in 50 ml of methanol p.a. is adjusted to pH 3 with a total of 28 ml of 2M methanolic HCl and stirred at room temperature. After 3 h, another 430 mg (6.84 mmol) of sodium cyanoborohydride are added. After a further 2 h, the reaction mixture is concentrated, adjusted to pH 9 with water and 6N KOH and extracted with dichloromethane. The organic phase is dried over sodium sulphate and concentrated in vacuo. The crude product is purified by column chromatography using dichloromethane/methanol (20:1).

Yield: 3.9 g (55.5% of theory), amorphous

EXAMPLE VI

4-Methoxyphenyl cyclopentyl ketone

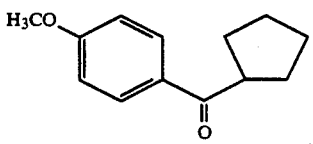

In analogy to the procedure of Example I, the title compound is prepared from 31 g (0.287 mol) of anisole, 46 g (0.345 mol) of aluminium chloride and 40 g (0.302 mol) of cyclopentanecarbonyl chloride.

Yield: 52.2 g (89% of theory), oil

EXAMPLE VII

4-Hydroxyphenyl cyclopentyl ketone

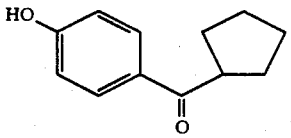

The title compound is prepared in analogy to the procedure of Example II from 30 g (0.147 mol) of the compound from Example VI and 290 ml of a 1M solution of boron tribromide (0.29 mmol) in dichloromethane.

Yield: 21.95 g (78.6% of theory), oil

EXAMPLE VIII 4-(Quinolin-2-yl-methoxy)phenyl cyclopentyl ketone

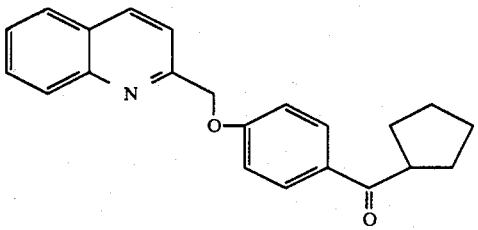

In analogy to the procedure of Example III, the title compound is prepared from 21.5 g (0.113 mol) of the compound from Example VII, 25 g (0.116 mol) of 2-chloromethylquinoline hydrochloride and 35.15 g (0.254 mol) of potassium carbonate.

Yield: 23 g (61.4% of theory), oil

EXAMPLE IX 4-(Quinolin-2-yl-methoxy)phenyl cyclopentyl ketoxime

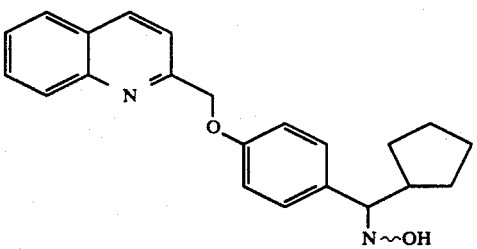

In analogy to the procedure of Example IV, the title compound is prepared from 20 g (60.3 mmol) of the compound from Example VIII and 6.3 g (90.7 mmol) of hydroxylamine hydrochloride.

Yield: 10.6 g (50.7% of theory)
M.p.: 174°–176° C.

EXAMPLE X

N-[4-(Quinolin-2-yl-methoxy)phenyl-cyclopentyl]methylhydroxylamine

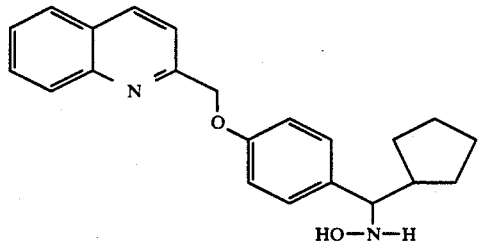

The title compound is prepared in analogy to the procedure of Example V from 6.15 g (17.8 mmol) of the compound from Example IX and 1.18 g (18.8 mmol) of sodium cyanoborohydride.

Yield: 3.0 g (48.5% of theory)
M.p.: 116°–117° C.

EXAMPLE XI

4-Methoxyphenyl cycloheptyl ketone

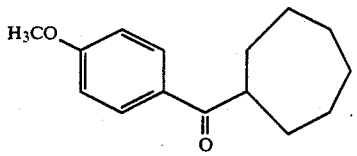

In analogy to the procedure of Example I, the title compound is prepared from 31.7 g (0.293 mol) of anisole, 47 g (0.352 mol) of aluminium chloride and 49.5 g (0.308 mol) of cycloheptanecarbonyl chloride.

Yield: 64.2 g (94.3% of theory), oil

EXAMPLE XII

4-Hydroxyphenyl cycloheptyl ketone

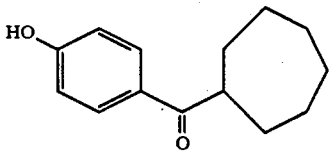

The title compound is prepared in analogy to the procedure of Example II from 53.2 g (0.229 mol) of the compound from Example XI and 458 ml of a 1M solution of boron tribromide (0.458 mol) in dichloromethane.

Yield: 34 g (68% of theory), oil

EXAMPLE XIII 4-(Quinolin-2-yl-methoxy)phenyl cycloheptyl ketone

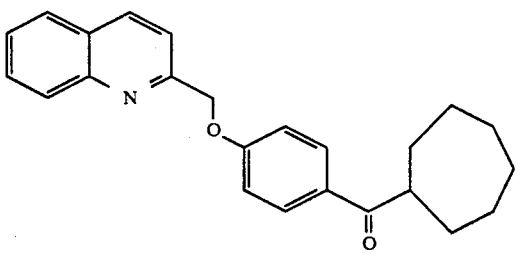

In analogy to the procedure of Example III, the title compound is prepared from 10 g (45.8 mmol) of the compound from Example XII, 10.3 g (48.1 mmol) of 2-chloromethylquinoline hydrochloride and 13.8 g (0.10 mol) of potassium carbonate.

Yield: 13.1 g (79.5% of theory)

EXAMPLE XIV

4(Quinolin-2-yl-methoxy)phenyl cycloheptyl ketoxime

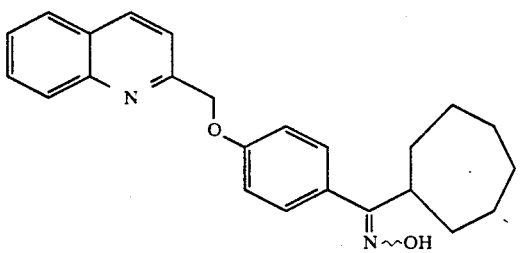

In analogy to the procedure of Example IV, the title compound is prepared from 12.9 g (35.9 mmol) of the compound from Example XIII and 3.75 g (53.9 mmol) of hydroxylamine hydrochloride.

Yield: 8.7 g (65%)
M.p.: 185°-186° C.

EXAMPLE XV

N-[4-(Quinolin-2-yl-methoxy)phenyl-cycloheptyl]methylhydroxylamine

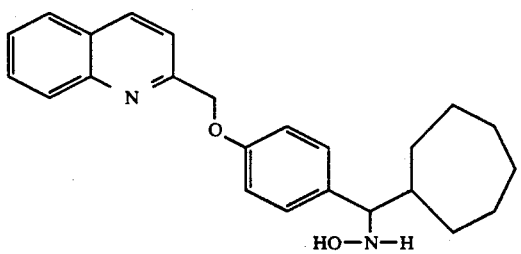

In analogy to the procedure of Example V, the title compound is prepared from 8.5 g (22.7 mmol) of the compound from Example XIV and 1.5 g (23.9 mmol) of sodium cyanoborohydride.

Yield: 2.6 g (30.4% of theory), amorphous

EXAMPLE XVI (+)-N-[Cyclohexyl-4-(quinolin-2-yl-methoxy)phenyl]-methylhydroxylamine, (1S)-(−)-camphanic acid salt

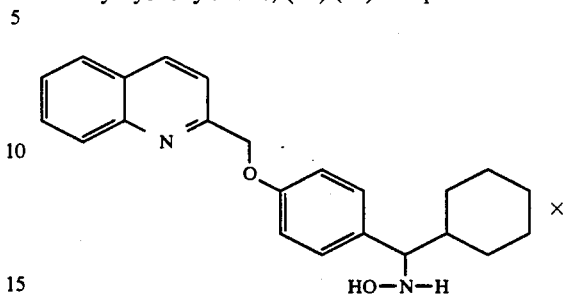

A solution of 5.25 g (0.026 mol) (1S)-(−)-camphanic acid in 16 ml methanol p.a. is added under reflux to a solution of 9.5 g (0.026 mol) of the compound of example V in 26 ml methanol p.a. After cooling to room temperature and after addition of some petrolether the title compound is crystallized. The crude product is recrystallized from 22 ml methanol p.a.

Yield: 2.6 g (17.6% of theory), colourless crystals
Melting point: 123°-125° C.
$[\alpha]^{20}_D = +6.5°$ (c=0.8 in DMSO)

EXAMPLE XVII (+)-N-[Cyclohexyl-4-(quinolin-2-yl-methoxy)phenyl]-methylhydroxylamine

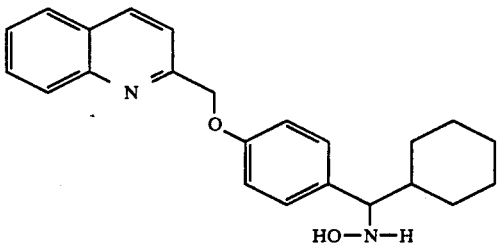

Process A

The enantiomerically pure title compound is separated from the racemate of example V by preparative NPLC on Chiracel Al) (Daicel) (eluent: petrolether/2-propanol/water/trifluoro acetic acid, 75:25:0.25:0.05).

Process B

To release the title compound from its salt 2.6 g (4.64 mol) of the compound of example XVI are partitioned between 20 ml 2N NaOH and 40 ml dichloromethane until a clear separation of the two phases is observed. The organic phase is dried over sodium sulphate. After concentration in vacuo the residue is recrystallized from diethyl ether.

Yield: 1.5 g (93.7% of theory), colourless crystals
Melting point: 100°-101° C.
enantiomeric excess: >99%
$[\alpha]^{20}_D = +10.5°$ (c=0.97 in DMSO)

In analogy to the procedures described above the compounds described in table 1 can be prepared.

TABLE 1

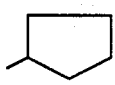

| Example No. | R¹ | enantiomere |
|---|---|---|
| XVIII | 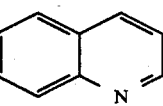 | (+) |
| XIX | 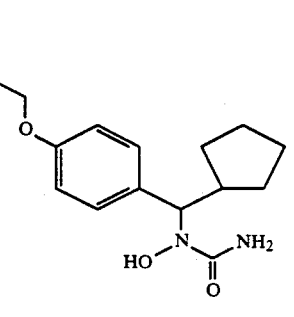 | (−) |
| XX | 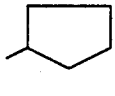 | (−) |
| XXI | 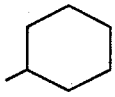 | (+) |
| XXII | 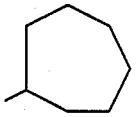 | (−) |

PREPARATION EXAMPLES

Example 1

N-[4-(Quinolin-2-yl-methoxy)phenyl-cyclohexyl]methyl-N-hydroxyurea

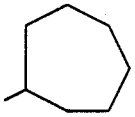

0.94 g (8.13 mmol) of trimethylsilyl isocyanate is added dropwise under an argon atmosphere at room temperature to a solution of 2.7 g (7.45 mmol) of N-[4-(quinolin-2-yl-methoxy)phenyl-cyclohexyl]methylhydroxylamine in 25 ml of dioxane p.a. The reaction mixture is heated at 100° C. under an argon atmosphere for 2.5 h, cooled to room temperature and treated with saturated ammonium chloride solution. It is extracted several times with ether, and the organic phase is dried over sodium sulphate and concentrated in vacuo. The product is obtained after column chromatography on silica gel using dichloromethane/methanol (9:1).

Yield: 1.3 g (43.0% of theory) of colourless crystals
M.p.: 166°-167° C. (decomposition)

Example 2

N-[4-(Quinolin-2-yl-methoxy)phenyl-cyclopentyl]-methyl-N-hydroxyurea

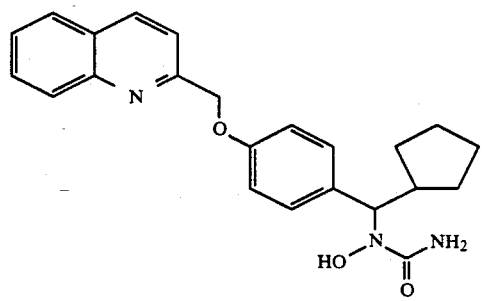

1.22 g (10.6 mmol) of trimethylsilyl isocyanate are added dropwise under an argon atmosphere at room temperature to a solution of 3.35 g (9.61 mmol) of N-[4-(quinolin-2-yl-methoxy)phenyl-cycloheptyl]methylhydroxylamine in 70 ml of methylene chloride p.a. The reaction mixture is stirred at room temperature for 2 h and concentrated in vacuo. The product is purified by column chromatography on silica gel using dichloromethane/methanol (20:1).

Yield: 2.8 g (74.4% of theory) of colourless crystals
M.p.: 165°-166° C. (decomposition)

Example 3

N-[4-(Quinolin-2-yl-methoxy)phenyl-cycloheptyl]-methyl-N-hydroxyurea

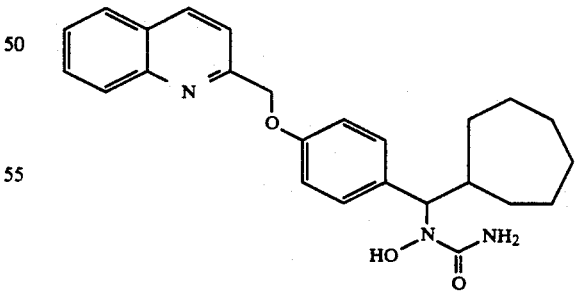

In analogy to the procedure of Example 2, the title compound is prepared from 2.3 g (6.11 mmol) of the compound from Example XV and 0.77 g (6.68 mol) of trimethylsilyl isocyanate.

Yield: 1.55 g (56% of theory) of colourless crystals
M.p.: 138°-140° C. (decomposition)

Example 4

(+)-N-[Cyclohexyl-4-(quinolin-2-yl-methoxy)phenyl]-methyl-N-hydroxyurea

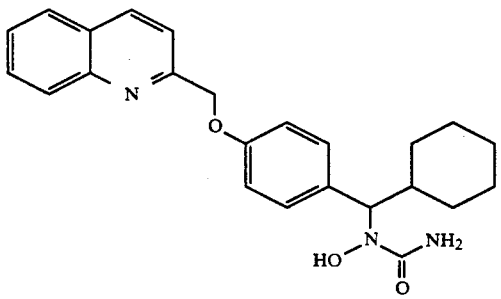

1.3 ml (10.2 mmol) trimethylsilyl isocyanate is dropped at room temperature to a solution of 1.5 g (4.1 mmol) of the compound of example XVII in 15 ml dichlormethane p.a. The reaction mixture is stirred 2 hours at room temperature. After washing with water, the organic phase is dried over sodium sulphate and concentrated in vacuo. The crude product is recrystallized from ethanol.

Yield: 1.0 g (59.5% of theory), colourless crystals
Melting point: 190°–192° C.
Enantiomeric excess: >99%
$[\alpha]^{20}_D = +38.8°$ (c=0.87 in DMSO)

In analogy to the procedure above the compounds described in table 2 can be prepared.

TABLE 2

| Example No. | R¹ | enantiomere |
|---|---|---|
| 5 | cyclopentyl | (+) |
| 6 | cyclopentyl | (−) |
| 7 | cyclohexyl | (−) |
| 8 | cycloheptyl | (+) |

TABLE 2-continued

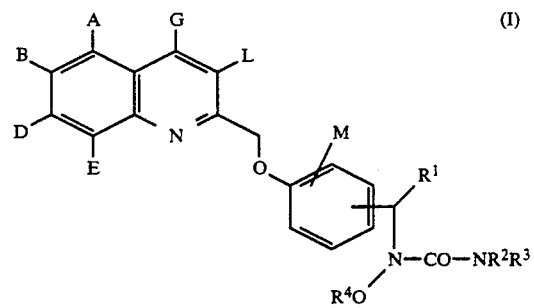

| Example No. | R¹ | enantiomere |
|---|---|---|
| 9 | cycloheptyl | (−) |

It will be appreciated that the instant specification and claims as set forth by way of illustration and not limitation, and that various modifications and changes may be made without departing from the spirit and scope of the present invention.

What we claim is:

1. Quinolin-2-yl-methoxybenzylhydroxyureas of the general formula (I)

in which
A, B, D, E, G, L and M are identical or different and represent hydrogen, hydroxyl, halogen, cyano, carboxyl, nitro, trifluoromethyl, trifluoromethoxy or represent straight-chain or branched alkyl or alkoxy each having up to 8 carbon atoms, or represent aryl having 6 to 10 carbon atoms, which is optionally substituted by halogen, hydroxyl, nitro or cyano, $R^1$ represents cycloalkyl or -alkenyl having 3 to 12 carbon atoms, represents straight-chain or branched alkyl having up to 8 carbon atoms, $R^2$ and $R^3$ are identical or different and represent hydrogen, straight-chain or branched alkyl having up to 8 carbon atoms or represent phenyl or benzyl, or $R^2$ represents hydrogen and
$R^3$ represents a group of the formula $-SO_2R^5$, in which $R^5$ denotes straight-chain or branched alkyl having up to 8 carbon atoms, which is optionally substituted by halogen, nitro, cyano, hydroxyl, trifluoromethyl or by aryl having 6 to 10 carbon atoms, or denotes aryl having 6 to 10 carbon atoms, which is monosubstituted to trisubstituted by identical or different substituents from the series comprising halogen, nitro, cyano, hydroxyl, straight-chain or branched alkyl, alkylthio or alkoxy having up to 8 carbon atoms, trifluoromethyl and trifluoromethoxy, R⁴ represents hydrogen or straight-chain or branched acyl having up to 8 carbon atoms or benzoyl, and their salts.

2. Quinolin-2-yl-methoxybenzylhydroxyureas according to claim 1 in which

A, B, D, E, G, L and M are identical or different and represent hydrogen, hydroxyl, fluorine, chlorine, bromine, carboxyl, nitro, trifluoromethyl, trifluoromethoxy or represent straight-chain or branched alkyl oralkoxy each having up to 6 carbon atoms, or represent phenyl which is optionally substituted by fluorine, chlorine, bromine, hydroxyl, nitro or cyano, R¹ represents cyclobutyl, cyclopentyl, cyclohexyl, cycloheptyl or cyclooctyl, represents straight-chain or branched alkyl having up to 6 carbon atoms, R² and R³ are identical or different and represent hydrogen or straight-chain or branched alkyl having up to 6 carbon atoms, or R² represents hydrogen and R³ represents a group of the formula —SO₂R⁵, in which R⁵ denotes straight-chain or branched alkyl having up to 6 carbon atoms, which is optionally substituted by fluorine, chlorine, nitro, cyano, hydroxyl or by phenyl, or denotes phenyl which is optionally monosubstituted or disubstituted by identical or different substituents from the series comprising fluorine, chlorine, bromine, nitro, cyano, hydroxyl, straight-chain or branched alkyl, alkylthio or alkoxy having up to 6 carbon atoms, trifluoromethyl and trifluoromethoxy, R⁴ represents hydrogen or straight-chain or branched acyl having up to 6 carbon atoms or benzoyl and their salts.

3. Quinolin-2-yl-methoxybenzylhydroxyureas according to claim 1 in which

A, B, D, E, G, L and M are identical or different and represent hydrogen, hydroxyl, fluorine, chlorine, bromine or straight-chain or branched alkyl having up to 4 carbon atoms, R¹ represents cyclopentyl, cyclohexyl or cycloheptyl, represents straight-chain or branched alkyl having up to 4 carbon atoms, R² and R³ are identical or different and represent hydrogen or straight-chain or branched alkyl having up to 4 carbon atoms, or R² represents hydrogen, and R³ represents a group of the formula —SO₂R⁵, in which R⁵ denotes straight-chain or branched alkyl having up to 4 carbon atoms, which is optionally substituted by fluorine, chlorine or phenyl, or denotes phenyl which is optionally substituted by fluorine, chlorine, bromine or by straight-chain or branched alkyl having up to 4 carbon atoms, R⁴ represents hydrogen or straight-chain or branched acyl having up to 4 carbon atoms or benzoyl and their salts.

4. Quinolin-2-yl-methoxybenzylhydroxyureas according to claim 1 in which the radical —HC(R¹)N(OR⁴)(CO—NR²R³) is in the 4-position relative to the quinolylmethoxy radical.

5. A compound according to claim 1, wherein such compound is N-[4-(quinolin-2-yl-methoxy)phenylcyclohexyl]methyl-N-hydroxyurea of the formula

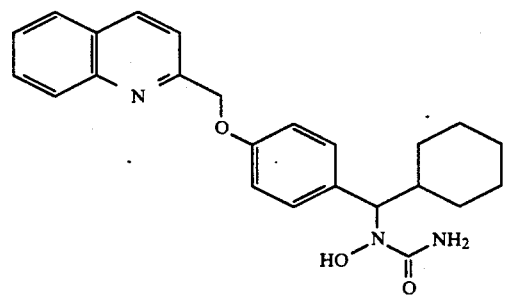

or a salt thereof.

6. A compound according to claim 1, wherein such compound is N-[4-(quinolin-2-yl-methyl)phenylcyclopentyl]methyl-N-hydroxyurea of the formula

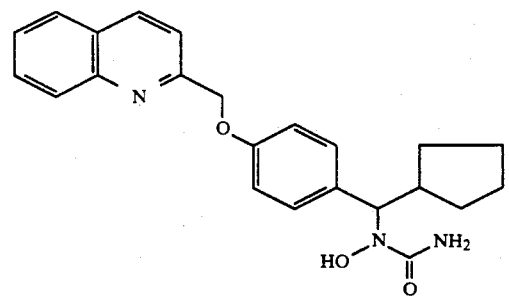

or a salt thereof.

7. A compound according to claim 1 wherein such compound is N-[4-(quinolin-2-yl-methoxy)phenylcycloheptyl]methyl-N-hydroxyurea of the formula

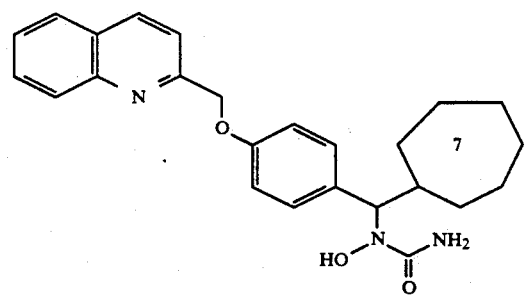

or salt thereof.

8. A composition for inhibiting lipsxygenase comprising an amount effective therefor of a compound of a salt thereof according to claim 1 and a pharmacologically acceptable diluent.

9. The method of inhibiting lipsxygenase in a patient in need thereof which comprises administering to such patient an amount effective therefor of a compound according to claim 1 or a salt thereof.

* * * * *

UNITED STATES PATENT AND TRADEMARK OFFICE
CERTIFICATE OF CORRECTION

PATENT NO. : 5,231,103

DATED : July 27, 1993

INVENTOR(S) : Matzke, et al.

It is certified that error appears in the above-identified patent and that said Letters Patent is hereby corrected as shown below:

Col. 22, line 60   Delete " lipsxygenase " and substitute -- lipoxygenase --

Col. 22, line 64   Delete " lipsxygenase " and substitute -- lipoxygenase --

Signed and Sealed this

Twenty-second Day of November, 1994

Attest:

BRUCE LEHMAN

*Attesting Officer*            *Commissioner of Patents and Trademarks*